(12) United States Patent
Fleischmann

(10) Patent No.: US 11,129,750 B2
(45) Date of Patent: *Sep. 28, 2021

(54) WOUND DRESSING

(71) Applicant: Biowim Products GmbH, Kirchzarten (DE)

(72) Inventor: Wilhelm Fleischmann, Freiburg (DE)

(73) Assignee: Biowim Products GmbH, Kirchzarten (DE)

(*) Notice: Subject to any disclaimer, the term of this patent is extended or adjusted under 35 U.S.C. 154(b) by 593 days.

This patent is subject to a terminal disclaimer.

(21) Appl. No.: 16/028,009

(22) Filed: Jul. 5, 2018

(65) Prior Publication Data

US 2018/0318136 A1    Nov. 8, 2018

Related U.S. Application Data

(63) Continuation of application No. 14/996,763, filed on Jan. 15, 2016, now Pat. No. 10,292,870, which is a
(Continued)

(30) Foreign Application Priority Data

Jul. 15, 2013   (DE) .................... 10 2013 107 464.2

(51) Int. Cl.
*A61F 13/00*   (2006.01)
*A61L 15/42*   (2006.01)
(Continued)

(52) U.S. Cl.
CPC .. *A61F 13/00063* (2013.01); *A61F 13/00017* (2013.01); *A61F 13/00046* (2013.01);
(Continued)

(58) Field of Classification Search
CPC ................... A61F 13/00–00085; A61L 15/425
See application file for complete search history.

(56) References Cited

U.S. PATENT DOCUMENTS 5,973,221 A * 10/1999 Collyer ............. A61F 13/00034
602/46
6,359,189 B1   3/2002 Fleischmann
(Continued)

FOREIGN PATENT DOCUMENTS

CN    101687058    3/2010
DE    102009005363    7/2010
(Continued)

OTHER PUBLICATIONS

Cazander et al., "Maggot therapy for wound healing: clinical relevance, mechanisms of action and future prospects," J Wound Technology, No. 5, Jul. 2009, pp. 18-23.
(Continued)

*Primary Examiner* — Susan S Su
(74) *Attorney, Agent, or Firm* — Akerman LLP; Peter A. Chiabotti

(57) ABSTRACT

A wound dressing in the form of a bag enclosing fly maggots, having a porous wall made from plastic, the wall having a membrane made from an open cell polyurethane foam, the pore diameter of which is approximately 0.1 mm to approximately 1 mm.

23 Claims, 4 Drawing Sheets

Related U.S. Application Data continuation-in-part of application No. PCT/EP2014/064267, filed on Jul. 3, 2014.

(51) Int. Cl.
*A61L 15/26* (2006.01)
*A61L 15/40* (2006.01)

(52) U.S. Cl.
CPC ............... *A61L 15/26* (2013.01); *A61L 15/40* (2013.01); *A61L 15/425* (2013.01)

(56) References Cited

U.S. PATENT DOCUMENTS

| | | |
|---|---|---|
| 6,555,729 B1 | 4/2003 | Fleischmann |
| 6,770,794 B2 | 8/2004 | Fleischmann |
| 7,816,577 B2 | 10/2010 | Aali |
| 9,168,324 B2 | 10/2015 | Mager et al. |
| 2007/0142757 A1 | 6/2007 | Aali |
| 2007/0191754 A1 | 8/2007 | Aali |
| 2008/0102106 A1 | 5/2008 | D'Haese et al. |
| 2009/0018480 A1 | 1/2009 | Mager |
| 2010/0042034 A1 | 2/2010 | Riesinger |
| 2010/0178320 A1 | 7/2010 | Westin |
| 2010/0262090 A1 | 10/2010 | Riesinger |
| 2011/0196329 A1 | 8/2011 | Eckstein et al. |
| 2011/0201715 A1 | 8/2011 | Schoenberger et al. |
| 2012/0046588 A1 | 2/2012 | Eckstein et al. |
| 2012/0136323 A1* | 5/2012 | Stasko .................. A61L 15/425 604/290 |

FOREIGN PATENT DOCUMENTS

| | | |
|---|---|---|
| DE | 102009042791 | 4/2011 |
| EP | 1020197 | 3/2003 |
| EP | 2014314 | 1/2009 |
| GB | 2422315 | 7/2006 |
| JP | 2009-131451 | 6/2009 |
| JP | 2010-531189 | 9/2010 |
| JP | 2010-532691 | 10/2010 |
| JP | 2012-500869 | 1/2012 |
| WO | 2006054108 | 5/2006 |

OTHER PUBLICATIONS

Patent Cooperation Treaty, "International Search Report" and translation thereof, issued in International Application No. PCT/EP2014/064267, by European Searching Authority, document of 8 pages, dated Mar. 12, 2014.

State Intellectual Property Office of the P.R.C., "Office Action" dated Aug. 7, 2017 for Chinese patent application No. 201480050844.5, document of 6 pgs.

"Reticulated Polyurethane Foam," https://www.ufpt.com/materials/foam/reticulated-polyurethane-foam.html, printed Feb. 2, 2018.

Japanese Patent Office, "Office Action" and English translation thereof dated Apr. 3, 2018 for Japanese patent application No. 2016-526516, document of 6 pgs.

* cited by examiner

WOUND DRESSING

CROSS-REFERENCE TO RELATED APPLICATIONS

This application is a continuation of Ser. No. 14/996,763, filed Jan. 15, 2016, which is a continuation-in-part of, and claims priority to PCT/EP2014/064267, filed Jul. 3, 2014, which claims priority to German Patent Application No. 10 2013 107 464.2, filed Jul. 15, 2013, the entireties of which are incorporated by reference herein.

BACKGROUND

The application relates to a wound dressing in the form of a bag enclosing fly maggots, having a porous wall made of plastic.

To treat chronic, poor-healing wounds, it is known to insert live fly maggots into the wound. For this purpose, preferably maggots of the blow fly, for example, of the *Lucilia sericata*, are used. The efficacy of the maggots is based on the wound cleaning (debridement), the anti-microbial activity and the stimulation of the wound healing. The digestive enzymes secreted by the maggots are substantially responsible for these effects.

The maggots can be inserted into the open wound as so-called free runners, an adhesive gauze net preventing them from escaping from the wound.

Today, an application of the maggots by way of a bag-shaped wound dressing in which the maggots are enclosed is preferred. The wall of the bag is porous so that the secretion secreted by the maggots can pass through into the wound and so that the dissolved necrotic tissue can enter the bag and can be taken up by the maggots. Such a wound dressing is known from the publication EP 1 020 197 B1.

In this known wound dressing, the wall is made of a fine-mesh net from polyamide (for example, nylon fibers) or polyester yarn having mesh widths of approximately 0.12 mm. The use of such wound dressings, which, for example, are marketed under the "BioBag" brand by the company Biomonde GmbH, Barsbüttel, Germany, is, for example, described in an article by G. Cazander et al., "Maggot therapy for wound healing . . . ," *Journal of Wound Technology*, July 2009, pages 18-23. In order to prevent an adhesive bonding of the walls, a spacer, for example, in the form of a PVA sponge, is preferably inserted into the bag, as a result of which sufficient room is kept free for the maggots.

In this known wound dressing, the textile net of the wall has to be very fine-meshed so that the maggots do not widen the mesh and escape. This fine-mesh structure has a disadvantageous effect on the porosity of the wall and, for this reason, on the fluid permeability of the wall. For this reason, it has been attempted to surround the bag made out of the fine-meshed polyamide net by a polyvinyl alcohol wet membrane. Such a wound dressing has been offered under the designation of "VitaPad" by the above-mentioned Biomonde GmbH. The PVA coating, however, in addition reduces the porosity. PVA foam finds application as a hydro sponge as a healing-promoting wound dressing. Owing to the strong evaporation, the water content of the PVA material as a coating can however only prevent a drying-out of the maggots in the short-term. For this reason, the entire bandage has to be moistened three times daily to keep the maggots alive. Moreover, the PVA membrane has to be kept wet because the membrane hardens when drying, no longer conforms to the wound and, as the case may be, harms the wound edges. The frequent moistening makes the wound treatment time-consuming. The evaporative cooling lowers the temperature of the bandage and, for this reason, of the wound, which negatively influences the growth of the maggots and the healing of the wound. In particular, the growth of microbial pathogens, so called wet germs, is promoted by constantly keeping the bandage wet. Infections caused hereby represent a dangerous complication of the wound treatment. For this reason, the application of this wound dressing is problematic, for reason of which said wound dressing has meanwhile been withdrawn from the market.

SUMMARY

The present disclosure provides a wound dressing which improves the efficacy and safety of the therapy using fly maggots.

The present application provides a wound dressing having the features and structures disclosed herein.

Advantageous embodiments and further developments are also disclosed herein.

DETAILED DESCRIPTION OF THE ILLUSTRATED EMBODIMENTS

Figure 1:
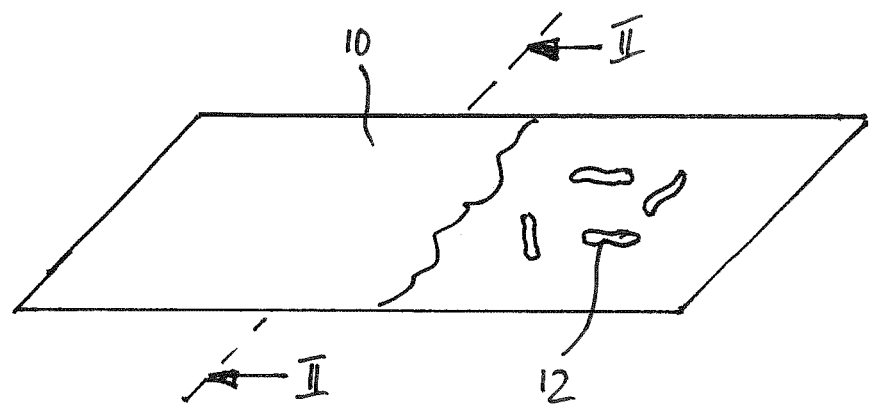
FIG. 1. illustrates one embodiment of a wound dressing in the form of a bag enclosing live fly maggots according to the present disclosure.
Figure 2:
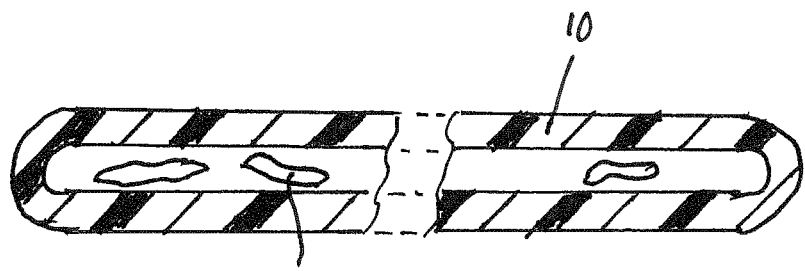
FIG. 2. illustrates a cross-sectional side view of the wound dressing of FIG. 1 taken along line II-II according to the present disclosure.

In FIGS. 1 and 2, according to the present disclosure, the wound dressing (10) is manufactured in form of a bag enclosing live fly maggots (12), having a wall which is made of a membrane made from totally open cell polyurethane foam (PUR foam). Preferably, the open cell structure of the PUR membrane is produced by reticulation. The totally consistently open cell structure ensures the fluid permeability of the wall of the bag. Preferably, the PUR foam is compressed after reticulation, as a result of which the stability of the foam material is increased and the pore size is reduced.

The use of an open cell PUR membrane offers surprising, substantial advantages vis-à-vis known wound dressings.

Clinical applications have surprisingly shown that it is possible to ensure optimal ambient conditions also for the maggots wrapped by the PUR dry membrane, provided that the membrane of the wound dressing directly rests on the wound surface. The evaporating surface of the PUR membrane is substantially smaller compared to the PVA wet membrane. For this reason, the moisture of the wound secretion in itself mostly suffices for the survival and growth of the maggots. The care-intensive wetting and wet-keeping of the wound bandage is, therefore, only required on occasion. The formation of wet germs is largely prevented.

While for wound dressings having a fine-mesh polyamide net a very small mesh width is necessary to prevent a widening of the mesh openings by the maggots, the PUR foam does practically not allow for a widening of the pore size by the maggots. For this reason, the membrane can be manufactured having a larger pore diameter and a smaller thickness, improving the permeability of the membrane for the maggot secretion and the liquefied necrotic tissue.

A further surprising advantage results from that the PUR foam may be manufactured having a very uniform pore size. For this reason, a membrane can be used, the pore diameter of which is selected at such a size that the maggots are just not able to penetrate into the pores. The manufacturing and processing technique of the PUR foam enables to reduce the scattering width of the pore size to such an extent that the secure enclosing of the maggots in the bag of the wound dressing is combinable with an optimal porosity of the membrane.

A further substantial advantage of the PUR membrane is in that this PUR membrane is soft and conforming so that the wound dressing abuts tightly against the surface of the wound, as a result of which the efficacy of the maggots and of the maggot secretion is promoted. In this instance, the soft flexural property of the PUR membrane is independent of ambient conditions, that is, particularly also of moisture. For this reason, it is not necessary to monitor and influence the moisture of the wound dressing. In doing so, the application is substantially simplified.

Figure 3:
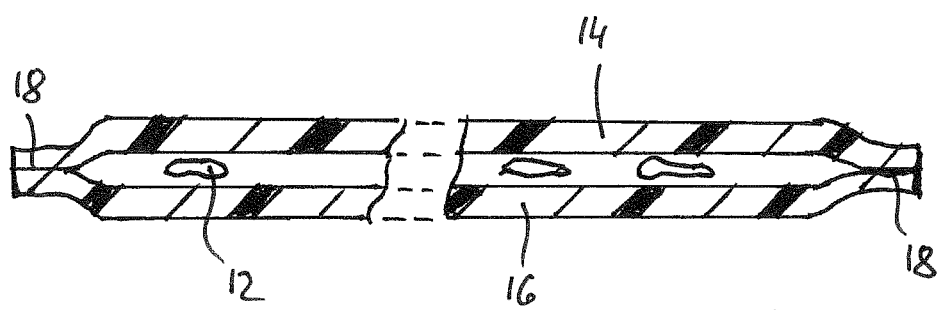
FIG. 3. illustrates a cross-sectional side view of another embodiment of wound dressing according to the present disclosure.

Another embodiment is shown in FIG. 3 where the bag-shaped wound dressing (10) is manufactured from two membrane surfaces (14, 16) placed one upon the other, which are connected to each other at the edges (18), for example, by adhesive bonding or welding. The seams at which the edges are connected with each other stay soft and flexural so that they do not compromise the abutting of the wound dressing against the wound surface and so that they do not damage the wound surface. The low melting point of PUR particularly enables a welding by simple, cost-effective means and a high reliability.

Owing to the material properties of PUR foam, the walls abutting each other in the interior of the bag do not have a tendency to adhesively bond. For this reason, the developing and growing maggots can push the soft and flexural walls of the bag apart and are not hindered in their development without having to additionally insert a spacer into the bag.

The coarse, thin membrane of the PUR foam has a relatively small surface so that the fluid evaporation is small. For this reason, there is a lower risk that the wound dressing and the enclosed maggots dry out.

The polyurethane foam can be produced based on polyether or polyester. The PUR foam of the membrane has a similarly healing-promoting influence onto the wound as it is known from PVA dressings. A PUR foam based on polyether is to be preferred because of its excellent resistance to hydrolysis, its resistance to acids and bases, its excellent flexibility in low temperatures and, in particular, because of its resistance to microbes.

The membrane made of the PUR foam can be manufactured having a thickness, that is, a wall thickness, of approximately 0.5 mm or less. Preferably, the thickness of the membrane can be approximately 0.1 mm. This low thickness promotes the soft flexural property of the membrane and the good fluid permeability.

The diameter of the pores of the PUR membrane is selected as great as possible to ensure a fluid permeability as great as possible on the side of the wound and a good ventilation of the maggots on the outer side. The upper limit of the pore diameter is determined by the size and, in particular, the diameter of the maggots. The diameter of the pores is chosen a little smaller than the diameter of the maggots so that the maggots cannot penetrate into the pores, expand the pores and escape through the wall.

In the case of the green bottle fly *Lucilia sericata*, the fly eggs have, for example, an average diameter of 0.47 mm. In the first larval stage, the newly hatched maggots have an average diameter of approximately 0.75 mm, a strong variation of +/−50% being observed. In the second larval stage, the maggots have an average diameter of 1.37 mm, here only smaller variations of +/−20% being observed.

It results from these values that the pore diameter of the PUR membrane is to be at least approximately 0.1 mm. A smaller pore diameter would only reduce the fluid permeability; however, it would not have any advantage for enclosing the maggots. The upper limit of the pore diameter for all potentially considered fly maggots should not exceed approximately 1.0 mm. Corresponding with the above mentioned measurements of the maggots, an upper limit of the pore size diameter of approximately 0.4 mm can be used for the maggots of the *Lucilia sericata* employed in most cases today. In order to reliably prevent the maggots from penetrating into the pores with their somewhat tapered head section, a pore diameter of approximately 0.3 mm is preferably chosen.

Figure 4:
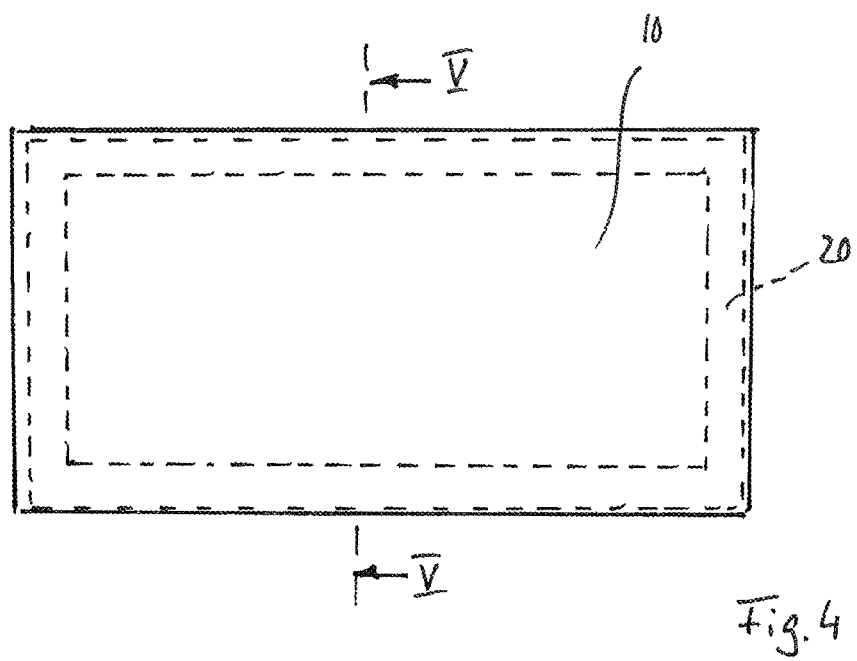
FIG. 4. illustrates another embodiment of a wound dressing with a frame-shaped spacer according to the present disclosure.
Figure 5:
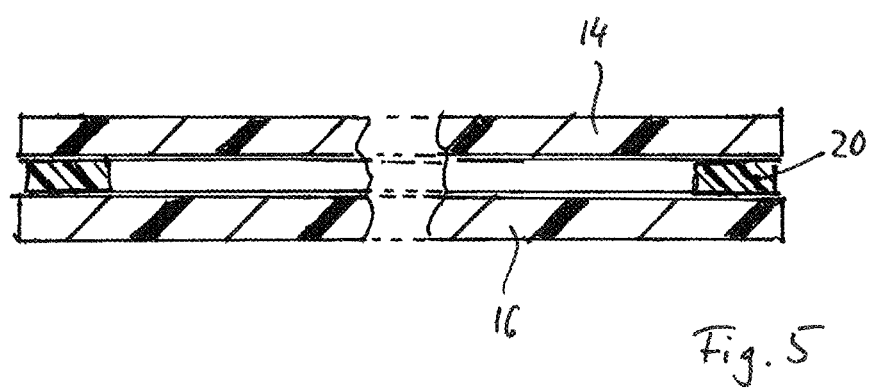
FIG. 5 illustrates a cross-sectional side view of the wound dressing of FIG. 4 taken along line V-V according to the present disclosure.

Another embodiment of a wound dressing is illustrated in FIGS. 4 and 5. To provide sufficient space for the maggots developing in the bag of the wound dressing, a frame-shaped spacer (20) can be inserted in the area of the interconnected edges of the membrane surfaces (14, 16) forming the wall of the bag. This spacer (20) increases the clear, inner distance of the walls; however, it does not reduce the inner surface area of the bag.

Figure 6:
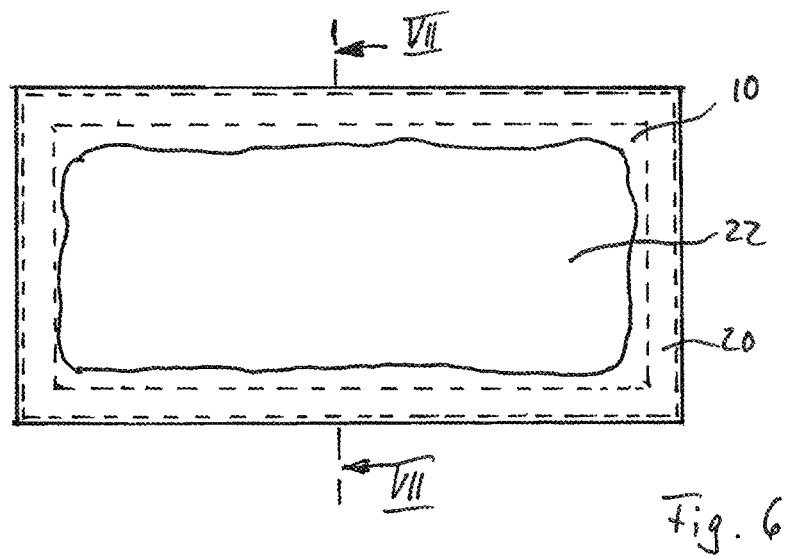
FIG. 6. illustrates another embodiment of a wound dressing with an additional inner bag according to the present disclosure.
Figure 7:
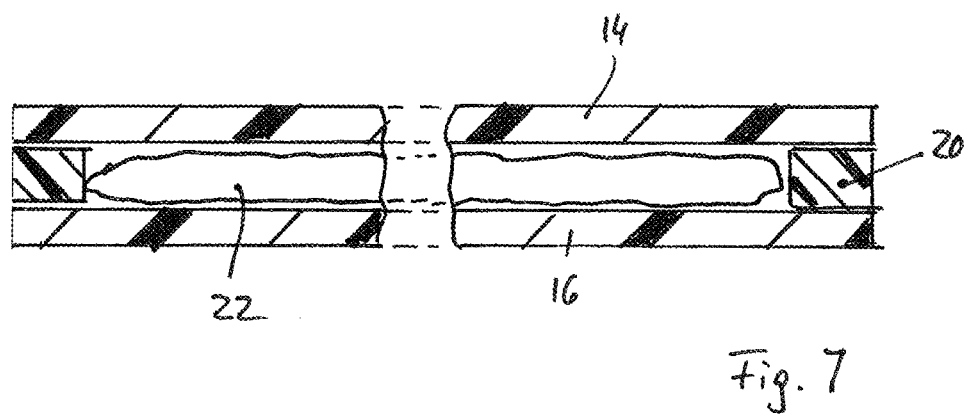
FIG. 7 illustrates a cross-sectional side view of the wound dressing of FIG. 6 taken along line VII-VII according to the present disclosure.
Figure 8:
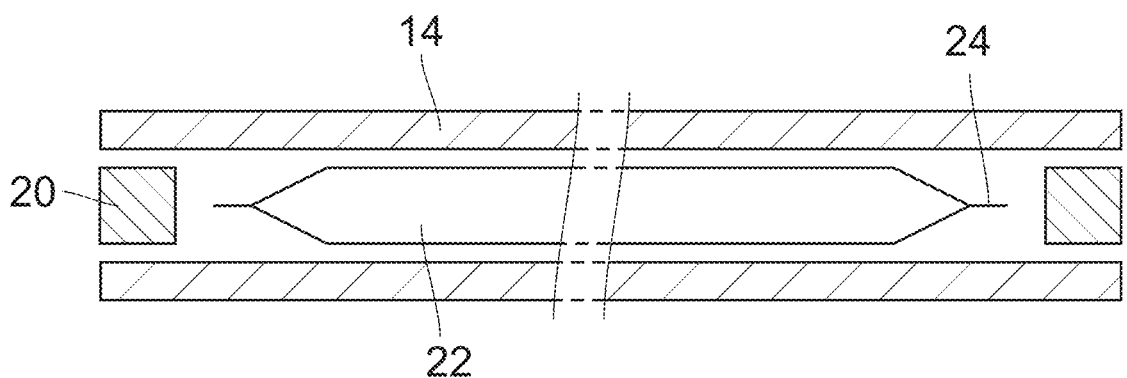
FIG. 8 illustrates another embodiment of a wound dressing with an additional inner bag according to the present disclosure.

FIG. 6 and FIG. 7 illustrates another embodiment of a wound dressing. In this embodiment, an additional inner bag (22) can be inserted into the bag (10) formed by the PUR membrane. This wall of additional inner bag (22) is also made out of a membrane from open cell PUR foam. The pore diameter of the PUR membrane of the inner bag (22) can be ≤0.4 mm. The membrane of the inner bag (22) has a low tear resistance. As shown in the embodiment in FIG. 8, the low tear resistance can be achieved in that the membrane of the inner bag has very thin walls and/or predetermined breaking lines (24). Such predetermined breaking lines (24) can, for example, be the welding or adhesive bonding seams at the edge of the inner bag.

In this embodiment, the eggs of the fly are inserted into the inner bag (22), which then is wrapped by the outer bag (10). The pore size of the inner bag ensures that the fly eggs cannot slip out of the inner bag (22). Owing to this pore size, the tiny maggots hatching from the eggs also cannot escape from the inner bag (22). After hatching, the maggots quickly increase in strength and size so that they produce a high pressure in the inner bag (22) leading to a tearing or bursting of the inner bag (22). Then, the maggots can roam freely in the outer bag (10). In this embodiment, the pore size of the PUR membrane of the outer bag (10) can be chosen corresponding to the size of the maggots escaping from the inner bag in the second larval stage. For this reason, the pore size of the wall of the outer bag can, for example, have a diameter of approximately 1.0 mm. This embodiment has the advantage that the maggots can be inserted already as eggs into the wound dressing and can actively contribute to the healing of the wound already during the earlier first larval stage. In the second larval stage, the maggots are then kept in the outer bag, which can have a considerably larger pore diameter and, therefore, a very high permeability. In this manner, the changing activity of the maggots during the course of the development of the maggots and the changing composition of the maggot secretion can be optimally utilized over the entire development duration of the maggots.

What is claimed is:

1. A wound dressing, comprising:
   a bag in which fly maggots can be enclosed, the bag having a porous wall made from plastic;
   wherein the porous wall has a membrane made from an open cell polyurethane foam, the pore diameter of which is less than or equal to 0.4 mm;
   wherein the polyurethane foam is reticulated;
   wherein the polyurethane foam is compressed; and
   wherein the pore diameter is approximately 0.3 mm.

2. The wound dressing according to claim 1, wherein the membrane has a thickness of less than or equal to 0.5 mm.

3. The wound dressing according to claim 2, wherein the thickness of the membrane is approximately 0.1 mm.

4. The wound dressing according to claim 1, wherein the bag comprises two membrane surfaces placed one upon the other and connected with each other at an edge of the bag.

5. The wound dressing according to claim 4, further comprising a frame-shaped spacer located between the membrane surfaces in an area of the connected edges of the membrane surfaces.

6. The wound dressing according to claim 4, wherein the two membrane surfaces are connected by adhesive bonding, welding or both.

7. The wound dressing according to claim 1, further comprising an outer bag in which the bag is inserted.

8. The wound dressing according to claim 7, wherein the outer bag has a pore diameter of approximately 0.4 mm to approximately 1.0 mm.

9. The wound dressing according to claim 1, wherein the polyurethane foam is based on polyether.

10. The wound dressing according to claim 1, wherein the polyurethane foam is based on polyester.

11. A wound dressing, comprising:
    a bag in which fly maggots can be enclosed, the bag having a porous wall;
    wherein the porous wall has a membrane made from a foam, the pore diameter of which is less than or equal to 0.4 mm;
    wherein the foam is reticulated;
    wherein the foam is compressed; and
    wherein the membrane has a thickness of less than or equal to 0.5 mm.

12. The wound dressing according to claim 11, further comprising a spacer located in the bag.

13. The wound dressing according to claim 11, wherein the bag comprises two membranes connected to each other at edges of the two membranes.

14. A wound dressing, comprising:
    an outer bag, the outer bag having a porous outer wall, wherein the porous outer wall is made from an outer bag foam;
    an inner bag in which fly maggots can be enclosed, the inner bag located inside the outer bag;
    wherein the inner bag has an inner bag wall; and
    wherein the inner bag wall is made of an inner bag foam with an inner bag foam pore diameter of less than 0.4 mm.

15. The wound dressing according to claim 14, wherein the inner bag foam is reticulated.

16. The wound dressing according to claim 14, wherein the inner bag foam is compressed.

17. The wound dressing according to claim 14, wherein the inner bag has breaking lines.

18. The wound dressing according to claim 14, wherein the outer bag foam has an outer bag foam pore diameter of approximately 0.1 mm to approximately 1.0 mm.

19. A wound dressing, comprising:
    a bag in which fly maggots can be enclosed, the bag having a porous wall made from plastic;
    wherein the porous wall has a membrane made from an open cell polyurethane foam, the pore diameter of which is less than or equal to 0.4 mm;
    wherein the polyurethane foam is reticulated;
    wherein the polyurethane foam is compressed; and
    wherein the membrane has a thickness of less than or equal to 0.5 mm.

20. The wound dressing according to claim 19, wherein the pore diameter is approximately 0.3 mm.

21. A wound dressing, comprising:
    a bag in which fly maggots can be enclosed, the bag having a porous wall made from plastic;
    wherein the porous wall has a membrane made from an open cell polyurethane foam, the pore diameter of which is less than or equal to 0.4 mm;
    wherein the polyurethane foam is reticulated;
    wherein the polyurethane foam is compressed;
    wherein the bag comprises two membrane surfaces placed one upon the other and connected with each other at an edge of the bag; and
    a frame-shaped spacer located between the membrane surfaces in an area of the connected edges of the membrane surfaces.

22. The wound dressing according to claim 21, wherein the membrane has a thickness of less than or equal to 0.5 mm.

23. A wound dressing, comprising:
    a bag in which fly maggots can be enclosed, the bag having a porous wall made from plastic;
    wherein the porous wall has a membrane made from an open cell polyurethane foam, the pore diameter of which is less than or equal to 0.4 mm;
    wherein the polyurethane foam is reticulated;
    wherein the polyurethane foam is compressed;
    an outer bag in which the bag is inserted; and
    wherein the outer bag has a pore diameter of approximately 0.4 mm to approximately 1.0 mm.

* * * * *